United States Patent [19]
Dupuis et al.

[11] Patent Number: 5,679,329
[45] Date of Patent: Oct. 21, 1997

[54] COSMETIC COMPOSITION FOR HOLDING THE HAIRSTYLE, CONTAINING A MILK PROTEIN AND/OR MILK PROTEIN HYDROLYSATE AND A KERATIN HYDROLYSATE

[75] Inventors: Christine Dupuis, Paris; Claude Dubief, Le Chesnay, both of France

[73] Assignee: L'Oreal, Paris, France

[21] Appl. No.: 295,895

[22] PCT Filed: Mar. 8, 1993

[86] PCT No.: PCT/FR93/00223

§ 371 Date: Sep. 8, 1994

§ 102(e) Date: Sep. 8, 1994

[87] PCT Pub. No.: WO93/17656

PCT Pub. Date: Sep. 16, 1993

[30] Foreign Application Priority Data

Mar. 9, 1992 [FR] France ................... 92 02776

[51] Int. Cl.⁶ ............................................. A61K 7/06
[52] U.S. Cl. ............... 424/70.14; 424/401; 424/DIG. 1; 424/DIG. 2; 424/47
[58] Field of Search ................... 424/401, 70.14, 424/DIG. 1, DIG. 2, 47, 535; 530/827, 832

[56] References Cited

U.S. PATENT DOCUMENTS

| | | | |
|---|---|---|---|
| 3,959,463 | 5/1976 | Nersesian et al. | 424/70.13 |
| 4,195,077 | 3/1980 | Marsh et al. | 424/70.14 |
| 4,275,748 | 6/1981 | Graziano | 132/202 |
| 4,423,032 | 12/1983 | Abe et al. | 424/70.12 |
| 4,517,175 | 5/1985 | Iwabuchi et al. | 424/70.14 |
| 4,530,829 | 7/1985 | Abe | 424/70.14 |
| 4,839,168 | 6/1989 | Abe et al. | 424/74 |
| 4,895,722 | 1/1990 | Abe et al. | 424/70.14 |
| 4,906,460 | 3/1990 | Kim et al. | 424/70.14 |
| 4,970,067 | 11/1990 | Panandiker et al. | 424/70.51 |
| 5,053,218 | 10/1991 | Shernov | 424/47 |

FOREIGN PATENT DOCUMENTS

| | | |
|---|---|---|
| 334776 | 9/1989 | European Pat. Off. . |
| 2041963 | 9/1980 | United Kingdom . |
| 8905629 | 6/1989 | WIPO . |
| 9114418 | 10/1991 | WIPO . |

*Primary Examiner*—John C. Bleutge
*Assistant Examiner*—Robert H. Harrison
*Attorney, Agent, or Firm*—Cushman Darby & Cushman Intellectual Property Group of Pillsbury Madison & Sutro LLP

[57] ABSTRACT

A cosmetic hair-perming composition with a cosmetically acceptable medium containing at least one milk protein and/or milk protein hydrolysate and at least one keratin hydrolysate having a molecular weight of 100–200,000.

18 Claims, No Drawings

COSMETIC COMPOSITION FOR HOLDING THE HAIRSTYLE, CONTAINING A MILK PROTEIN AND/OR MILK PROTEIN HYDROLYSATE AND A KERATIN HYDROLYSATE

The present invention relates to a cosmetic composition intended for use for holding the hair, containing a milk protein and/or milk protein hydrolysate and a keratin hydrolysate.

Milk proteins or their hydrolysates have already been used in compositions for holding the hair. They endow the hair with good shape-retention and, contrary to other proteins and keratins, they do not give rise to a phenomenon Of making the hair sticky. These compositions possess, however, the drawback of causing a phenomenon of powdering on brushing the hair, which gives the hair an unattractive appearance. Moreover, milk proteins or their hydrolysates, when used in styling mousses, generate foams whose stability and expansion are insufficient.

The Applicant discovered, surprisingly, that combinations of some keratin hydrolysates with milk proteins and/or their hydrolysates endowed the hair with good shape-retention without causing stickiness or powdering of the hair.

Furthermore, the particular combinations of the invention, when used in styling mousses, possess a synergistic effect on the qualities of rigidity, stability and expansion, as well as a smaller aeration of the foams, relative to the components of these combinations taken individually.

The subject of the invention is hence a cosmetic composition for holding the hair, containing at least one milk protein and/or milk protein hydrolysate and at least one keratin hydrolysate.

Another subject of the invention consists of a process for the cosmetic treatment of hair, intended for promoting the holding thereof, consisting in applying to it the combination of at least one milk protein and/or milk protein hydrolysate and at least one keratin hydrolysate.

Other subjects of the invention will become apparent on reading the description and the examples which follow.

The cosmetic composition according to the invention is essentially characterized in that it contains, in a cosmetically acceptable medium, at least one milk protein and/or milk protein hydrolysate and at least one keratin hydrolysate of molecular weight between 100 and 200,000.

The keratin hydrolysates according to the invention are obtained by hydrolysis of animal or human keratins originating, for example, from materials such as hair, wool, skin, bristles, silks, feathers, scales, hooves or horn. They may be chemically modified and, in this case, bear quaternary ammonium groups at the end of their peptide chain or grafted on their peptide chain.

Among keratin hydrolysates used according to the invention, there may be mentioned, more especially:

keratin hydrolysates obtained by moderate hydrolysis of bovine hoof keratin of molecular weight approximately 100,000, such as the product sold under the name KERASOL by the company CRODA;

keratin hydrolysates obtained by controlled acid hydrolysis, of molecular weight approximately 150, such as the product containing 25% of active substance sold under the name CROTEIN HKP S/F by the company CRODA;

keratin hydrolysates bearing, on the peptide chain, quaternary ammonium groups containing at least one $C_{10}$–$C_{18}$ fatty chain, such as the product sold under the name CROQUAT WKP by the company CRODA.

According to the present invention, all milk proteins are usable, as well as the mixtures thereof and their hydrolysates. Milk contains essentially two types of protein, caseins and whey proteins, the main constituents of which are $\alpha$-lactalbumin, $\beta$-lactoglobulin and immunoglobulins.

The milk proteins which are usable according to the invention are preferably obtained from cow's milk or from milk by-products resulting, for example, from cheese- or buttermaking, such as whey or buttermilk.

These proteins may be concentrated and/or separated and dried by various traditional methods.

The following are used more especially:

caseins obtained from skimmed milk by precipitation, by acid treatment, by lactic fermentation or using rennet, and then dried. It is preferable to use soluble salts of caseins, obtained by neutralization, such as sodium, calcium or magnesium caseinates.

Such products are sold, for example, by the companies DE MELKINDUSTRIE VEGHEL BV, ARMOR PROTEINES, UNION LAITIERE NORMANDE (U.L.N.);

whey proteins, separated from whey by various processes such as ultrafiltration, electrodialysis, ion exchange chromatography, size exclusion chromatography.

Such products are sold, for example, by the company ARMOR PROTEINES under the name PROSERIC DF 90, by the company U.L.N. under the names ALBUVIR (HC86, HC86 NK, HC90), by the company ISIGNY under the name ISOPRO S'75.

buttermilk proteins such as those sold, for example, by the company ISIGNY under the name soft buttermilk containing 30% of active substance;

"total proteins" of milk, obtained from skimmed milk.

Such products are sold by the company DE MELKINDUSTRIE VEGHEL under the names MPC 75 and REFIT HPA or by the company ARMOR PROTEINES under the name LR 80F.

According to the present invention, the hydrolysates of these different proteins may also be used.

Casein hydrolysates are sold, for example, by the company ARMOR PROTEINES under the name PEPTIDES N3, by the company CRODA under the name HYDROLACTIN 2500.

Whey protein hydrolysates are sold by the company U.L.N. under the name SEROVIR HF, by the company ARMOR PROTEINES under the name PEPTIDES 80.

Hydrolysates of "total proteins" are sold by the company L.S.N, under the name LACTOLAN LS 5879, or by the company BROOKS under the name HYDROMILK 20.

The milk proteins and/or their hydrolysates are present in the compositions according to the invention in concentrations preferably of between 0.02 and 15% by weight relative to the total weight of the composition.

The keratin hydrolysates are present in the compositions according to the invention in concentrations preferably of between 0.1 and 10% by weight relative to the total weight of the composition.

The compositions according to the present invention can take the form of aqueous or aqueous-alcoholic lotions, optionally thickened, or gels. They may be packaged either in a pump bottle for application in the form of anatomization or spray, or packaged as an aerosol for application in the form of a spray,. and preferably in the form of a mousse.

The cosmetically acceptable medium can consist of water and/or a cosmetically acceptable organic solvent such as, more especially, monohydric alcohols having from 1 to 8 carbon atoms, for instance ethanol, isopropanol, benzyl alcohol, phenylethyl alcohol, or polyhydric alcohols such as alkylene glycols, for instance ethylene glycol, propylene glycol, used alone or mixed. The solvent is preferably present in proportions not exceeding 50% by weight relative to the total weight of the composition, and preferably from 5 to 30%.

The compositions according to the present invention can contain additives customarily used in cosmetics, compatible with the milk proteins or their hydrolysates and the keratin hydrolysates, chosen from emollients, lubricants, penetrating agents, stabilizers, perfumes, thickening agents, preservatives and, where appropriate, plasticizers, cationic agents, polymers, silicones or other, optionally quaternized animal or vegetable proteins.

The thickeners used in the compositions according to the invention are preferably chosen from acrylic acid polymers, crosslinked or otherwise, and more especially polyacrylic acids crosslinked with a polyfunctional agent such as products sold under the name CARBOPOL by the company GOODRICH, cellulose derivatives such as methyl cellulose, hydroxyethylcellulose, hydroxypropylmethyl-cellulose, the sodium salts of carboxymethylcellulose or high molecular weight ethylene/maleic anhydride copolymers.

These thickeners are preferably present at between 0.05 and 5%, and more especially between 0.1 and 2%, by weight relative to the total weight of the composition.

When the compositions according to the invention are packaged as an aerosol for application in the form of a spray or mousse, the propellent agents may be chosen from volatile hydrocarbons such as n-butane, propane, isobutane, or the mixtures thereof, or a mixture of these hydrocarbons with chlorinated and/or fluorinated hydrocarbons such as the compounds sold under the name FREON or DYMEL by the company DU PONT DE NEMOURS.

They may also be chosen from the chlorinated and/or fluorinated hydrocarbons described above and the mixtures thereof, carbon dioxide and nitrous oxide.

It is preferable, according to the invention, to use a mixture of n-butane, isobutane, propane and monofluorotrichloromethane, and more especially a mixture of n-butane, isobutane and propane.

In spray compositions, the propellent phase represents 20 to 80% of the total weight of the pressurized composition.

In the aerosol mousse compositions, the propellent phase represents from 2 to 15% of the total weight of the pressurized composition.

The compositions according to the invention are used for the shaping or for the fixing of hair. They may be applied as a treatment product after dyeing or bleaching, after shampooing or after permanent-waving or straightening of hair.

When the compositions according to the invention are used for the shaping of hair, the total concentration of milk protein or its hydrolysate and of keratin hydrolysates is preferably between 0.1 and 5%, and more especially between 0.2 and 2%, by weight relative to the total weight of the composition.

When the compositions are used for the fixing of hair, the total concentration of milk proteins and/or of their hydrolysates and of keratin hydrolysates is preferably between 0.2 and 15% by weight, and more especially between 0.5 and 10% by weight, relative to the total weight of the composition.

An especially preferred composition according to the invention consists of a composition for the shaping of hair in the form of an aerosol mousse.

The process for the cosmetic treatment of hair, intended for promoting the holding thereof, which constitutes another subject of the invention, consists in applying at least one milk protein and/or milk protein hydrolysate and at least one keratin hydrolysate in a cosmetically acceptable medium to wet or dried hair, by means of the compositions described above.

The examples which follow are intended to illustrate the invention, no limitation, however, being implied.

EXAMPLE 1

A styling mousse of the following composition is prepared:

| | | |
|---|---|---|
| Keratin hydrolysate of MW 100,000, sold in aqueous solution containing 15.4% of AS under the name KERASOL by the company CRODA | | 0.4 g AS |
| Mixture (80:20) of casein and whey proteins, sold containing 89.5% of AS under the name REFIT EPA by the company DE MELKINDUSTRIE VEGHEL | | 0.27 g AS |
| Quaternized soybean protein hydrolysate, sold containing 30% of AS under the name CROQUAT SOYA by the company CRODA | | 0.3 g AS |
| Perfume, colorant, preservative | qs | |
| Demineralized water | qs | 100 g |
| Aerosol packaging: | | |
| Above composition: | | 95 g |
| Ternary mixture of n-butane, isobutane >55%, propane, sold underthe name AEROGAZ 3,2 N by the company ELF AQUITAINE | | 5 g |
| | TOTAL | 100 g |

EXAMPLE 2

A fixing spray of the following composition is prepared:

| | | |
|---|---|---|
| Calcium caseinate sold containing 90.3% of AS under the name CALCIUM CASEINATE I by the company DE MELK-INDUSTRIE VEGREL | | 9.03 g AS |
| Keratin hydrolysate of mw 100,000, sold in aqueous solution containing 15% of AS under the name KERASOL by the company CRODA | | 3 g AS |
| Perfume, preservative | qs | |
| Demineralized water | qs | 100 g |

This composition is packaged in a pump bottle.

EXAMPLE 3

A styling gel of the following composition is prepared:

| | | |
|---|---|---|
| Quaternized keratin hydrolyzate, sold in aqueous solution containing 30% of AS under the name CROQUAT WKP by the company CRODA | | 0.3 g AS |
| Buttermilk proteins sold under the name BABEURRE DOUX [Soft Buttermilk] containing 30% of AS by the company ISIGNY | | 0.06 g AS |
| Crosslinked polyacrylic acid, sold under the name CARBOPOL 940 (MW 4,000,000) by the company GOODRICH | | 0.5 g |
| Triethanolamine | qs | pH 7 |
| Perfume, preservative | qs | |
| Demineralized water | qs | 100 g |

EXAMPLE 4

A styling mousse of the following composition is prepared:

| | |
|---|---|
| Keratin hydrolysate of MW 100,000, sold in aqueous solution containing 15% of AS under the name KERASOL by the company CRODA | 0.5 g AS |
| Calcium caseinate | 0.3 g AS |
| Perfume, colorant, preservative | qs |
| Demineralized water | qs 100 g |
| Aerosol packaging | |
| Above composition: | 90 g |
| Ternary mixture of n-butane, isobutane >55%, propane, sold under the name AEROGAZ 3,2 N by the company ELF AQUITAINE | 10 g |
| TOTAL | 100 g |

We claim:

1. Cosmetic composition intended for holding the hair which contains, in a cosmetic acceptable medium, from 0.02 to 15% by weight of at least one of milk protein and milk protein hydrolysate and from 0.1 to 10% by weight of keratin hydrolysate of weight average molecular weight between 100 and 200,000, relative to the total weight of the composition, wherein the keratin hydrolysate is obtained by hydrolysis of keratin originating from hair, wool, skin, bristles, silks, feathers, scales, hooves or horns, and can contain quaternary groups grafted on the peptide chain or at the end of the chain.

2. Composition according to claim 1, which further contains from 0.1 to 2% by weight, relative to the total weight of the composition, of a thickening agent selected from the group consisting of optionally crosslinked acrylic acid polymers, methylcellulose, hydroxyethylcellulose, hydroxypropyl methylcellulose, the sodium salts of carboxymethylcellulose and ethylene/maleic anhydride copolymers.

3. Composition according to claim 1, wherein the keratin hydrolysate is selected from the group consisting of:
  (i) hydrolysates of weight average molecular weight approximately 100,000 obtained by moderate hydrolysis of bovine hoof keratin;
  (ii) hydrolysates of weight average molecular weight approximately 150 obtained by controlled acid hydrolysis; and
  (iii) hydrolysates containing, on their peptide chain, quaternary ammonium groups comprising at least one $C_{10}$–$C_{18}$ fatty chain.

4. Composition according to claim 1 wherein the milk proteins are selected from the group consisting of casein and whey proteins obtained from cow's milk or from milk by-products resulting from cheese- or butter-making, and their hydrolysates.

5. Composition according to claim 1 wherein the milk proteins are selected from the group consisting of:
  (i) caseins obtained from skimmed milk by precipitation, by acid treatment, by lactic fermentation or using rennet, and then dried, and their hydrolysates;
  (ii) whey proteins, separated from whey by ultrafiltration, electrodialysis, ion exchange chromatography, size exclusion chromatography, and their hydrolysates;
  (iii) buttermilk proteins and their hydrolysates;
  (iv) so-called "total" proteins obtained from skimmed milk, and their hydrolysates;
  and mixtures thereof.

6. Composition according to claim 1 which is in the form of an optionally thickened aqueous or aqueous-alcoholic lotion or the form of a gel.

7. Composition according to claim 1, which is packaged in the form of a pump bottle for application in the form of an atomization or spray, or packaged as an aerosol for application in the form of a spray or mousse.

8. Composition according to claim 1 wherein the cosmetically acceptable medium contains water and/or an organic solvent selected from the group consisting of monohydric alcohols having 1 to 8 carbon atoms and polyhydric alcohols, used alone or mixed, said solvent being present in proportions not exceeding 50% by weight relative to the total weight of the composition.

9. Composition according to claim 1 which further contains additives compatible with the milk proteins, their hydrolysates and the keratin hydrolysates, selected from the group consisting of emollients, lubricants, penetrating agents, stabilizers, perfumes, thickening agents, preservatives, plasticizers, cationic agents, polymers, silicones and animal or vegetable proteins, optionally quaternized.

10. Composition according to claim 1 which further contains from 0.05 to 5% by weight, relative to the total weight of the composition, of a thickening agent selected from the group consisting of optionally crosslinked acrylic acid polymers, methylcellulose, hydroxyethylcellulose, hydroxypropyl methylcellulose, the sodium salts of carboxymethylcellulose and ethylene/maleic anhydride copolymers.

11. Composition according to claim 1, packaged as an aerosol for application in the form of a spray or mousse, which contains a propellant agent selected from the group consisting of n-butane, propane, isobutane, chlorinated hydrocarbons, fluorinated hydrocarbons, chlorinated and fluorinated hydrocarbons, mixtures thereof, carbon dioxide and nitrous oxide.

12. Composition according to claim 11, which contains a propellent agent selected from the group consisting of n-butane, isobutane, propane, monofluorotrichloromethane, and mixtures thereof.

13. Composition according to claim 11, packaged as an aerosol for application in the form of a spray, which contains from 20 to 80% by weight of propellent agent relative to the total weight of the composition.

14. Composition according to claim 11, packaged as an aerosol for application in the form of a mousse, which contains from 2 to 15% by weight of propellent agent relative to the total weight of the composition.

15. Composition according to claim 1 used for the shaping of hair or the fixing of hair as treatment product which can be applied after dyeing or bleaching, after shampooing or after permanent-waving or straightening of hair.

16. Composition according to claim 15 for the shaping of hair, wherein the total concentration of milk protein or of milk protein hydrolysates and of keratin hydrolysate is between 0.1 and 5% by weight relative to the total weight of the composition.

17. Composition according to claim 15, for the fixing of hair wherein the total concentration of milk protein or of milk protein hydrolysate and of keratin hydrolysate is between 0.2 and 15% by weight relative to the total weight of the composition.

18. Process for the cosmetic treatment of hair, intended for promoting the holding thereof, wherein at least one milk protein or milk protein hydrolysate and at least one keratin hydrolysate of weight average molecular weight between 100 and 200,000 are applied in a cosmetically acceptable medium to wet or dried hair, by means of a composition as defined in claim 1.

* * * * *